United States Patent
Aiba et al.

(10) Patent No.: US 6,221,096 B1
(45) Date of Patent: Apr. 24, 2001

(54) INTRAVASCULAR STENT

(75) Inventors: Mitsuru Aiba, Fujisawa; Shin Ishimaru, Tokyo, both of (JP)

(73) Assignee: Kanto Special Steel Works, Ltd., Fujisawa (JP)

( * ) Notice: Subject to any disclaimer, the term of this patent is extended or adjusted under 35 U.S.C. 154(b) by 0 days.

(21) Appl. No.: 09/242,110

(22) PCT Filed: Jun. 8, 1998

(86) PCT No.: PCT/JP98/02524

§ 371 Date: Feb. 9, 1999

§ 102(e) Date: Feb. 9, 1999

(87) PCT Pub. No.: WO98/56449

PCT Pub. Date: Dec. 17, 1998

(30) Foreign Application Priority Data

Jun. 9, 1997 (JP) .................................................. 9-151372

(51) Int. Cl.⁷ ........................................................ A61F 2/06
(52) U.S. Cl. ........................ 623/1.11; 623/1.23; 623/1.16; 606/108
(58) Field of Search ................................. 623/1.11, 1.12, 623/1.18, 1.19, 1.16, 1.23, 1.3, 1.31; 608/108

(56) References Cited

U.S. PATENT DOCUMENTS

| 5,035,706 | * | 7/1991 | Giantureo et al. ................... 606/198 |
| 5,405,377 | | 4/1995 | Cragg . |
| 5,549,635 | * | 8/1996 | Solar ..................................... 606/198 |
| 5,665,115 | | 9/1997 | Cragg . |
| 5,683,448 | | 11/1997 | Cragg . |
| 5,690,643 | * | 11/1997 | Wijay .................................... 606/108 |
| 5,733,325 | * | 3/1998 | Robinson et al. ....................... 623/1 |
| 5,759,186 | * | 6/1998 | Bachmann et al. .................. 606/108 |
| 5,766,237 | | 6/1998 | Cragg . |
| 5,843,167 | | 12/1998 | Dwyer et al. . |
| 6,168,616 | * | 1/2001 | Brown, III .......................... 623/1.11 |

FOREIGN PATENT DOCUMENTS

| WO 95/00178 | * | 1/1994 | (EP) ................................... 623/1.11 |
| 7/24072 | | 1/1995 | (JP) . |
| 7/500272 | | 1/1995 | (JP) . |
| 7/47134 | | 2/1995 | (JP) . |
| 8/502428 | | 3/1996 | (JP) . |
| 8/299456 | | 11/1996 | (JP) . |
| 8/511437 | | 12/1996 | (JP) . |

* cited by examiner

Primary Examiner—David H. Willse
Assistant Examiner—Suzette J. Jackson
(74) Attorney, Agent, or Firm—Wenderoth, Lind & Ponack, LLP.

(57) ABSTRACT

An intravascular stent 11 has an elastic self-expandable cylindrical stent proper 12. The stent proper 12 is connected to metal support wires 18 that are long enough to reach outside of the body of a patient through a catheter 31. Manipulation of the support wires 18 pushes the stent proper 12 into a blood vessel from within the catheter, thereby allowing it to expand there, and then contracts and retracts the stent proper 12 into the catheter 31, repeatedly.

6 Claims, 2 Drawing Sheets

INTRAVASCULAR STENT

FIELD OF THE INVENTION

This invention relates to self-expandable intravascular stents for use in the treatment of ectatic vascular diseases (such as aneurysm) and more particularly to intravascular stent catheters that not only expand on their own when they are pressed in from outside the body but also can be afterward constricted and recovered.

BACKGROUND OF THE INVENTION

An aneurysm is an unfavorable condition resulting from arterial sclerosis, inflammation and other causes that will grow larger and lead to fatal ruptures when left unattended. Since current medicinal treatments hardly produce any good results, excision and replacement of dilatations have conventionally been resorted to. However, this condition appears frequently in aged persons and is often associated with the disturbances of many organs (such as the brain, heart and liver). Therefore, applicability of surgical operations, which can often cause exorbitant stresses, is limited. Thus, intravascular treatments using catheters whose operative stresses are relatively moderate have been receiving the attention of the world. The use of stents is one of such treatments in popular use.

The stent is a term to generally denote artificial tubular structures that are inserted into blood vessels and other tubular organs in the body to support them. When, for example, stricture or other defamation has occurred in blood vessels, gallbladers, gullets, bowels, ureters and other internal tubular organs, a stent is inserted into them to prevent the recurrence of such stricture or deformation by supporting them. Generally, the main body of the stent is elastic, being made of metal wires or other similar materials. The main body of the stent is designed so that it can radially expand and constrict repeatedly. The stent is often inserted in the body using a catheter. Therefore, the stent must become smaller than the inside diameter of the catheter when it constricts so that it can be contained within the catheter. When released from inside the catheter, the stent must radially expand to the desired diameter.

Several types of self-expanding stents having elastic tubular shapes are made of wires of stainless steel, shape memory alloy or other metals and are intended for use in blood vessels for the treatment of aneurysm, as disclosed, for example, in Japanese Provisional Patent Publications Nos. 24072 and 47134 of 1995 and Japanese Provisional Patent Publications Nos. 500272 of 1995 and 299456, 502428 and 511437 of 1996. These self-expanding stents are mainly used as stent grafts (the term graft denotes an artificial blood vessel inserted into a human blood vessel) that are sutured and fixed in laminar polyester blood vessels. A stent graft compressed and loaded in a thin catheter is pressed into an aneurysm from a part of a peripheral artery (mainly the femoral artery by way of the catheter). The stent graft is then allowed to expand on its own and dwell in the aneurysm to achieve both occlusion of the dilatation and repair of vascular flow. The intravascular treatment using stent grafts causes only mild operative stresses, thus lightening burdens of stresses imposed on patients and being applicable to wider varieties of aneurysms than conventional methods. This treatment is now very effective for cases of aneurysms.

To securely close an aneurysm by the use of an indwelling stent graft, it is necessary to keep the stent tightly fitted in the artery by ensuring that the stent covers not only the aneurysm itself but also the normal arteries at its center and on its peripheries. However, this can sometimes block up main arteries branching from the aneurysm and nearby sound aortas, which can lead to other organ derangements. The renal, inferior mesenteric and hypogastric arteries are the main visceral arteries affected by the dominal aneurysm. Occlusion of these arteries can lead to renal and intestinal ischemic dysfunctions. With aneurysms of the thoracic aorta, occlusion of the intercostal artery can cause disturbance of the spinal cord blood flow which, in turn, can result in a serious complication called paraplegia (lower-body motor paralysis).

However, the intravascular stents proposed so far cannot be re-constricted and recovered after they have been once released from catheters and allowed to expand on their own. As such, they present a serious problem in that they cannot be recovered from within the blood vessel even after an organ or blood flow derangement has occurred. In addition, if they have been placed in the wrong place, they are difficult to move to the right place for correction. Thus, their applicability is limited by safety considerations.

The object of this invention is to provide a stent that can be re-constricted and recovered after it has been released from a catheter and allowed to expand on its own.

SUMMARY OF THE INVENTION

An intravascular stent according to this invention comprises a self-expandable cylindrical stent proper that is connected to metal support wires having a long enough length to be extendable to outside the body via a catheter. Manipulation of the support wires pushes the stent proper from within the catheter into a blood vessel, allows it to repeatedly expand and collapse therein and return into the catheter.

Another intravascular stent according to this invention comprises a collapsible and expandable stent inserted in a catheter in a collapsed state that is adapted to be pushed out from the leading end of the catheter to a given position in a blood vessel. This intravascular stent comprises a stent proper, which, in turn, comprises an elastic, collapsible and expandable cylinder made of metal wires and multiple connecting wires spaced around the circumference of the elastic cylinder, extending along the longitudinal axis of the elastic cylinder so as to intersect with the metal wires constituting the elastic cylinder and fastened to the elastic cylinder at the points of intersection with the metal wires thereof, and support wires extending backward from the stent proper and throughout the entire length of the catheter.

The catheter contains the stent in a collapsed condition. In administering medical treatment, the catheter is driven to the desired position in a blood vessel of a patient, and then the stent proper is pushed out from within the catheter into the blood vessel by pressing the support wires from outside the body of the patient. The stent proper pushed out from the catheter expands on account of its own elasticity. To leave the stent proper temporarily in the blood vessel, the whole of the stent proper is retracted back into the catheter by pulling the support wires from outside the body after a given time. When the support wires are pulled, the support wires and stent proper contract at the exit end of the catheter. The stent proper can be repeatedly expanded and contracted and pushed out from and retracted back into the catheter. The stent is thus brought exactly to the desired point.

At least one of the stent proper and support wires may have a superelastic deformable part made of nickel-titanium-based alloy or other shape-memory alloy wires that exhibit superelasticity substantially at 37° C. Shape-memory alloys have a superelastic property that exhibits an elastic limit 15 to 20 times higher than that of ordinary metals above a certain temperature. Because of this superelastic property, shape-memory alloys are suited for the manufacture of best-quality stents that can maintain the original shape even after repeating release and retraction many times. This superelasticity appears above a certain specific temperature called the transformation temperature indigenous to each material. The shape-memory alloys suited for the stents should have a transformation temperature that is controlled so that superelasticity appears at least at 37° C. (body temperature).

The stent proper can be fastened by stitching to artificial blood vessels made of polyester films, thereby increasing the affinity between the stent and living body.

This invention permits placing a recoverable temporary stent in the target position for a certain limited time before placing a permanent stent there, thereby permitting prediction of risks that might be involved with the placement of the permanent stent and making appropriate judgement. After confirming that there is no risk, the temporary stent is recovered and a conventional permanent stent is placed in the target position to carry out the desired treatment safely. The result is a significant increase in safety. This invention also permits applying stents to abdominal aneurysms directly under the renal artery, hypogastric artery aneurysms, distal thoracic aorta aneurysms, thoracoabdominal aortic aneurysm and other aneurysms with which conventional permanent stents have been risky and difficult to use. This invention has thus solved the problem of limited applicability of conventional stents. Accordingly, this invention has expanded the applicability of intravascular medical treatments employing stent grafts producing lighter surgical stresses to aneurysms to which they have conventionally been inapplicable. Stents have not only alleviated the pains and burdens of patients, but also made effective medical treatments available to a large number of aneurysm patients.

PREFERABLE EMBODIMENTS OF THE INVENTION

Figure 1:
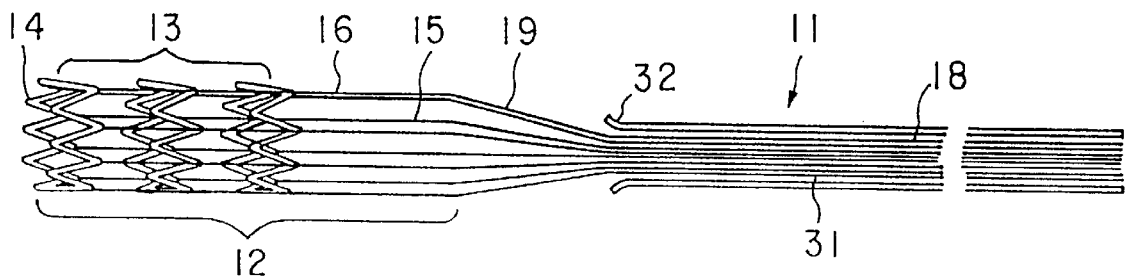
FIG. 1 shows an embodiment of a recoverable temporary stent according to this invention, with a stent proper in an expanded condition.
Figure 2:
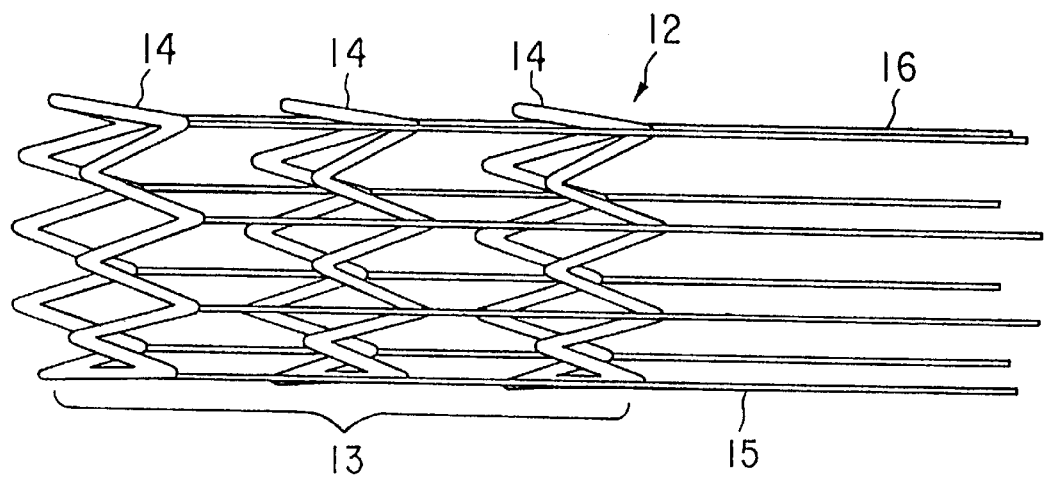
FIG. 2 shows details of the leading end of the stent proper shown in FIG. 1.

FIG. 1 schematically shows a recoverable temporary stent according to this invention, with the stent proper in an expanded condition. FIG. 2 schematically shows details of the leading end of the stent proper shown in FIG. 1. As can be seen, the leading end of a stent 11 constitutes a stent proper 12 and support wires 18 extend backward from the rear end of the stent proper 12.

The stent proper 12 comprises multiple elastic rings 14 (for example, three in the illustrated embodiment) formed by bending zigzag-shaped metal wires annularly. The elastic rings 14 are spaced apart from each other in the longitudinal direction. Multiple connecting wires 15 (for example, eight in the illustrated embodiment) are disposed at equal intervals around the periphery of the elastic rings 14 and welded or brazed to the elastic rings 14 at the at the points of intersection therewith, thereby forming an elastic cylinder 13. The preferable number of the elastic rings 14 is two to four. The connecting wires 15 extending behind the elastic cylinder 13 form a parallel segment 16.

The connecting wires 15 extending backward from the rear end of the parallel segment 16 of the stent proper 12 are bundled together as the support wires 18. Each of the connecting wires 15 and support wires 18 is a single continuous wire of shape-memory alloy. The outside diameter of the bundle of the support wires 18 is somewhat smaller than the inside diameter of the catheter 31. The support wires 18 are long enough to pass through the catheter 31 and permit manipulation of the stent 12 placed in the desired position from outside the body. In the illustrated embodiment, the support wires 18 are a bundle of metal wires continuing from the connecting wires 15. Instead, a single wire or cord may be used as a support wire 18. It is preferable that the support wires 18 are three to eight in number. The stent proper 12 and support wires 18 have high enough rigidity to withstand extrusion from and retraction into the catheter 31 by manipulation from outside. Being made of multiple metal wires circumferentially spaced apart and bundled together, the support wires 18 remain unbent even when pressed from outside.

In an expanded condition, the stent proper 12 in the stent 11 has an outside diameter of 20 to 40 mm and a length of 30 to 100 mm. The elastic rings 14, connecting wires 15 and support wires 18 should preferably be made of stainless steel, titanium and shape-memory alloys. The elastic rings 14, connecting wires 15 and support wires 18 may be made of the same material or different materials. Only such members as are required to maintain the desired shape may be made of shape-memory alloys. Nickel-titanium-based shape-memory alloys are most suited for stents because of their outstanding superelasticity and good corrosion resistance. The metal wires constituting the elastic rings 14, connecting wires 15 and support wires 18 are approximately 0.4 to 0.8 mm in diameter. The stent proper 12 may also be made of a cylinder of coil springs or wire netting fastened with multiple connecting wires.

The stent proper 12 in the stent 11 described above is contracted and contained in the catheter 31. In giving a medical treatment or a surgical operation, the catheter 31 is brought to a desired position in a blood vessel. Then, the stent proper 12 is pushed out from within the catheter 31 into the blood vessel by pushing the support wires 18 from outside the body. Being made of multiple metal wires circumferentially spaced apart and bundled together, the support wires 18 remain unbent even when pressed from outside. The stent proper 12 pushed out of the catheter 31 expands on its own because of the elasticity of the elastic rings 14. With the expansion of the elastic rings 14, the leading end 19 of the support wires 18 becomes flared. When the stent proper 12 is temporarily left in the blood vessel, the stent proper 12 is placed in the desired position, and then, after a desired period of time, the support wires 18 are pulled from outside the body. The leading end 18 of the support wires 17 and the stent proper 12 are smoothly contracted at the outwardly curved exit end 32 of the catheter 31 and retracted therein.

Figure 3:
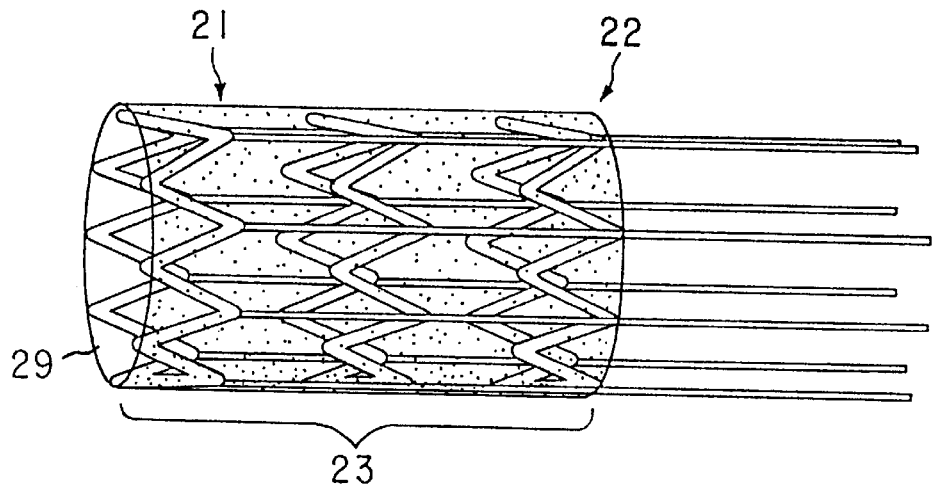
FIG. 3 shows details of the leading end of a temporary stent fastened by stitching to an artificial blood vessel made of ultra-thin polyester film.
Figure 4:
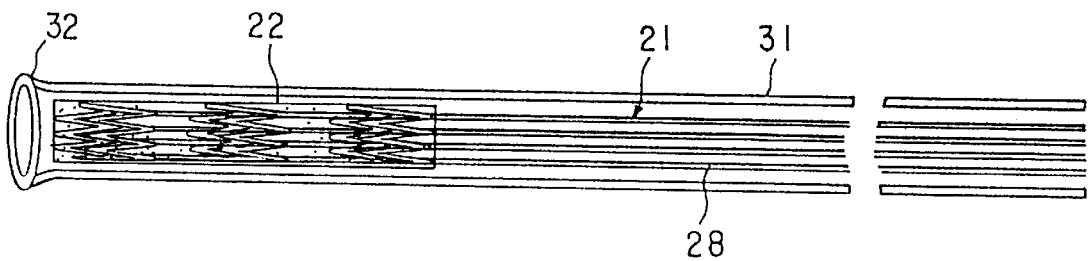
FIG. 4 shows the temporary stent shown in FIG. 3 contained in a catheter.
Figure 5:
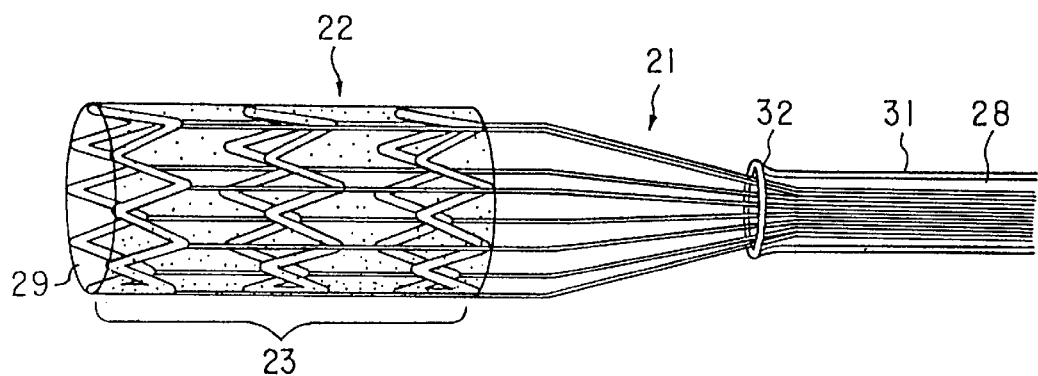
FIG. 5 shows the stent proper shown in FIG. 3 that is pushed out from the catheter and expanded by pushing support wires.

FIG. 3 shows another embodiment of this invention. A stent 21 comprises a stent proper 22 with an elastic cylinder 23 whose outer periphery is covered with, and fastened by stitching to, an artificial blood vessel (a graft) 29 of ultra-thin polyester film. FIG. 4 shows the stent proper 22 folded in the catheter 31. FIG. 5 shows the stent proper 22 released from the catheter 31 and expanded by pushing the support wires 28.

The structure of this embodiment is similar to that of the one shown in FIG. 1, except that the elastic cylinder 23 constituting the stent proper 22 is covered with the graft 29. The elastic cylinder 23 and graft 29 are stitched together. The graft 29 is made of fabrics of polyester, Teflon (a trademark for polytetrafluoroethylene) and polyurethane fibers. On being contracted radially, the elastic cylinder 23 covered with the graft 29 can be contained in the catheter 31, with the diameter thereof becoming smaller than the inside diameter of the catheter 31. The stent proper 22 is designed to be expandable to have an outside diameter of approximately 20 to 40 mm so that it can sufficiently expand blood vessels of any diameter when being pushed out of the catheter 31.

An example of application of a recoverable temporary stent according to this invention to the treatment of an aneurysm of the thoracic aorta is described below.

In the treatment, the stent graft stitched to an artificial blood vessel (graft) of ultra-thin polyester film as shown in FIG. 3 was used. The expanded stent proper had an outside diameter of 30 mm and a length of 75 mm. The stent proper and support wires were both made of nickel-titanium-based shape-memory alloy wires whose transformation temperature was controlled so that the stent proper exhibits superelasticity at 37° C. (body temperature). Each of the support wires had an outside diameter of 0.5 mm and a length of 1 m. The inside diameter of the catheter was 4.0 mm.

The stent proper contracted and contained in the catheter was pushed into the inside of the aneurysm via the catheter sent from an dissected end of a peripheral artery (an aorta is chosen in most cases). The stent proper was allowed to expand on its own and left in the desired position. By leaving the stent proper in the desired position for a desired period of time, information about obstruction or hindrance to vascular flow was obtained to check if the placement of a permanent stent involved any risk. Because nonexistence of such risk was confirmed, the temporary stent was retracted into the catheter and recovered to the outside of the body by pulling the support wires connected to the stent proper from outside the body. Then, a permanent stent was inserted to the desired position. If any risk is predicted about the placement of a permanent stent, the temporary stent according to this invention is retracted into the catheter and moved to another position to find a safe position. As is obvious from the above, the recoverable temporary stent according to this invention permits operations on aortic aneurysms in a short time, with safety and certainty.

What is claimed is:

1. An intravascular stent adapted to be inserted into a catheter, said intravascular stent comprising:
    a cylindrical stent proper comprising:
        a connecting wire having a tail end and a leading end and comprising multiple metal wires disposed parallel to each other and circumferentially spaced from each other, and
        a plurality of short, diametrically expandable, cylindrical, elastic rings fastened to said leading end of said connecting wire at intervals along a length of said connecting wire, wherein said cylindrical stent proper is operable to automatically expand to a diameter greater than an inside diameter of the catheter when outside of the catheter; and
    a support wire extending from said tail end of said connecting wire of said cylindrical stent proper having a length long enough to pass through the catheter, said support wire being operable to allow proper placement of said cylindrical stent proper.

2. An intravascular stent according to claim 1, wherein at least one of said cylindrical stent proper and said support wire comprises a superelastic deformable segment made of shape-memory alloy wires exhibiting superelasticity substantially at 37° C.

3. An intravascular stent according to claim 1, further comprising an artificial blood vessel comprising a thin polyester film, wherein said cylindrical stent proper is fastened to said artificial blood vessel by stitching.

4. An intravascular stent adapted to be inserted into a catheter, said intravascular stent comprising:
    a cylindrical stent proper comprising:
        a connecting wire having a tail end and a leading end and comprising multiple metal wires disposed parallel to each other and circumferentially spaced from each other, and
        a plurality of short, diametrically expandable, cylindrical, elastic rings, each of which being formed of a metal wire bent in a zigzag fashion and fastened at a bent portion to said leading end of said connecting wire at intervals along a length of said connecting wire, wherein said cylindrical stent proper is operable to automatically expand to a diameter greater than an inside diameter of the catheter when outside of the catheter; and
    a support wire extending from said tail end of said connecting wire of said cylindrical stent proper having a length long enough to pass through the catheter, said support wire being operable to allow proper placement of said cylindrical stent proper.

5. An intravascular stent according to claim 4, wherein at least one of said cylindrical stent proper and said support wire comprises a superelastic deformable segment made of shape-memory alloy wires exhibiting superelasticity substantially at 37° C.

6. An intravascular stent according to claim 4, further comprising an artificial blood vessel comprising a thin polyester film, wherein said cylindrical stent proper is fastened to said artificial blood vessel by stitching.

* * * * *